United States Patent [19]

Howa

[11] 4,114,271
[45] Sep. 19, 1978

[54] VIBRATORY DENTAL TOOL

[75] Inventor: Scott P. Howa, Salt Lake City, Utah

[73] Assignee: Vibrabrush, Inc., Salt Lake City, Utah

[21] Appl. No.: 741,946

[22] Filed: Nov. 15, 1976

Related U.S. Application Data

[63] Continuation of Ser. No. 574,864, May 6, 1975, abandoned.

[51] Int. Cl.² .......................................... A61C 13/00
[52] U.S. Cl. ....................................................... 32/2
[58] Field of Search .............. 15/22; 32/57, 53, 40 R, 32/2

[56] References Cited

U.S. PATENT DOCUMENTS

| 368,948 | 8/1887 | Helmer | 32/53 |
| 2,874,470 | 2/1959 | Richards | 32/58 |
| 2,975,448 | 3/1961 | Glaser | 15/22 |
| 3,809,977 | 5/1974 | Balamuth | 32/58 |

Primary Examiner—Robert Peshock

[57] ABSTRACT

A vibratory dental tool is provided for use in the creation of crowns, bridges, plates and other forms of artificial teeth. The tool has receiving means in a housing for receiving and holding dental tool attachments, such as a soft brush, spatula or the like. A source of vibratory motion, preferably an electromagnet in combination with a vibratory plate, is disposed within the housing and connected by appropriate means to the attachment-receiving means to impart vibrational motion to the attachment and to the housing. Means are provided for adjusting the intensity of the vibrations.

4 Claims, 4 Drawing Figures

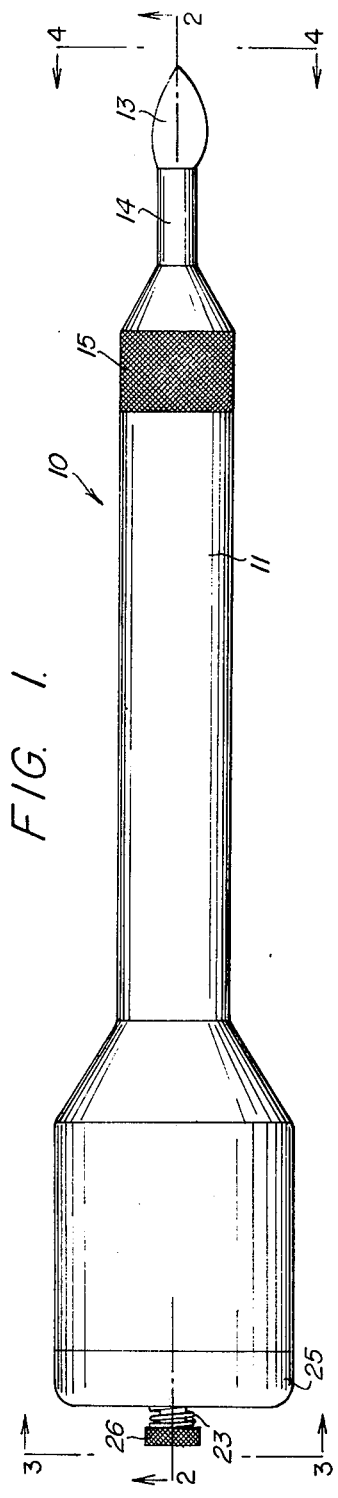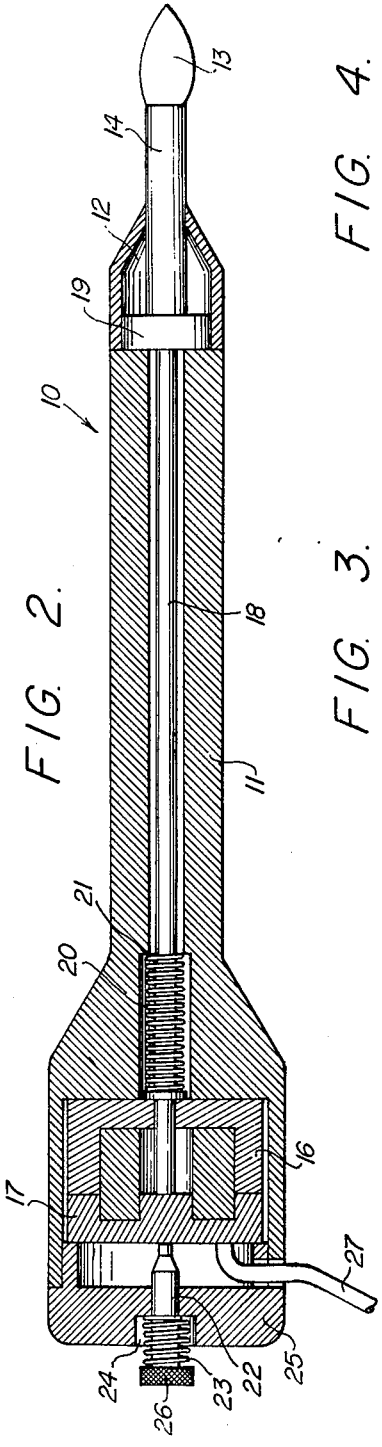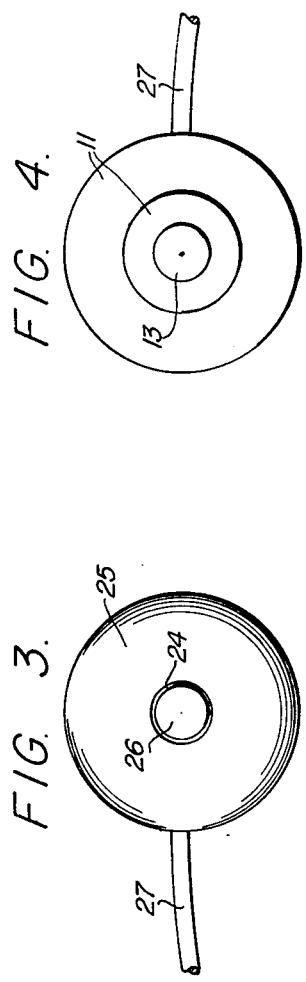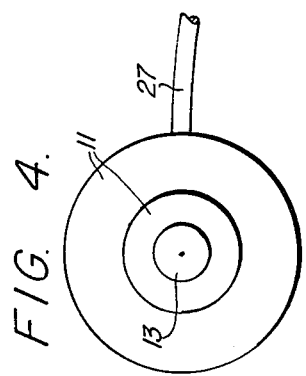

VIBRATORY DENTAL TOOL

This is a continuation of application Ser. No. 574,864, filed May 6, 1975 and now abandoned.

BACKGROUND OF THE INVENTION

The dental arts industry is concerned with the creation of dental replacements, including bridges, caps, crowns, dentures, and the like. Heretofore it has been the common practice in the industry to cast from a metal, such as gold, a crown or replacement tooth to which a ceramic or porcelain type material is applied to crate a natural appearing tooth. A common implement used by dental technicians in such dental appliances has been a small table-top vibrator. In practice, the dental technician takes a small pointed brush in his hand, adheres ceramic material to the tip of the brush and applies it to the metal substrate by resting his hand against the table-top vibrator.

As the ceramic is applied to the tooth with a brush, the vibrations from the vibrator are passed through the hand to the brush tip and aide in gently distributing the ceramic material about the surface of the tooth. The process is time consuming and extremely tedious for the dental technician, since it requires that the hand be held against the vibrator during application of the ceramic.

There has been a need for a dental tool of the type disclosed in the present application for aiding dental technicians in applying ceramic type material to metal substrates. The present invention overcomes the problems and inefficiencies characteristic of the equipment now in use in the dental industry. Patents in the so-called electric toothbrush field, such as U.S. Pat. Nos. 2,977,614; 3,166,943 and 3,379,906, are unrelated to the present invention, in that they are not adapted for use in the dental technology field, and in addition provide for rotary motion and/or longitudinally reciprocal motion of the toothbrush. Such motions are not desirable for the present invention, and in fact could not be employed in the dental technology field.

SUMMARY OF THE INVENTION

In accordance with the invention, a vibratory dental tool is provided for use by a dental technologist applying covering material in a paste or liquid form to a metallic substrate, such as a tooth base. The tool is preferably intended for use with a small pointed brush, such as is common in water color brushes, but may be used with other dental attachments such as a spatula, and the like.

The tool has a housing, preferably elongate and tubular for convenience of the dental technician, but can be of another shape serving the same objectives. The housing can be constructed of any suitable material, such as stainless steel, or hardened plastic. At one end of the housing is a receptacle adapted to receive and retain the attachment, such as a pointed brush, in a secure manner.

The housing also contains a vibrational source, such as an electromagnet coupled with a vibrational plate. As energy passes through the electromagnet, the energy alternately attracts and repels the adjacent plate to set up a series of vibrations within the plate. Means, such as an elongate rod, extend from the plate to the attachment for the purpose of passing the vibrational motion from the plate to the attachment. At the same time, the vibrations are passed to the housing itself, causing the housing to vibrate in addition to the attachment. Externally of the housing there is provided preferably a roughened surface which can be used to contact the tooth substrate, thereby imparting vibrations directly from the housing to the tooth substrate in order to cause the ceramic material to be distributed in a uniform thickness over the substrate.

Means are also provided for adjusting the intensity of the vibrations. In a preferred embodiment this includes a threaded screw extending through the housing in contact with the vibrational plate. Adjustment of the screw can increase or decrease the vibrational intensity as desired by the dental technician. The vibrational motion imparted by the vibration source means within the housing to the attachment and housing is best described as random vibration. By random it is intended to indicate that the motion is not rotational about any axis, nor is it reciprocal in the sense of the dental attachment reciprocating along a longitudinal axis.

In use, the tool is held by the dental technician and ceramic material is applied to the tooth substrate with the attachment, such as a brush or spatula. The vibrations from the tool are passed through the brush and aide in depositing the ceramic material evenly over the substrate surface. After sufficient ceramic material has been applied to the substrate, the roughened surface of the housing can be placed in contact with the substrate, causing the substrate to vibrate to distribute the ceramic material evenly about the substrate surface. The tool can be controlled by the foot pressure of a rheostat connected in line with the energy source to the vibrational source means within the housing. The rheostat can be used to start the tool and can be utilized to control the amount of energy, such as electrical power reaching the tool thereby controlling the vibrational intensity of the tool.

While the tool is primarily adapted for use in the dental technology field, it has obvious application in any field in which ceramic material is employed, such as art and other hobby crafts.

THE DRAWINGS

The best mode presently known for carrying out the invention is illustrated in the accompanying drawings, in which:

FIG. 1 is a side elevation of a preferred embodiment of the tool;

FIG. 2 repesents a side elevational section of the tool taken along the line 2—2 of FIG. 1;

FIG. 3 shows an end view of the tool taken along the line 3—3 of FIG. 1; and

FIG. 4 illustrates an opposite end view of the tool taken along the line 4—4 of FIG. 1.

DETAILED DESCRIPTION OF THE EMBODIMENT SHOWN IN THE DRAWING

As illustrated in FIGS. 1 and 2, the tool 10 is preferably encased in an oblong, tubular housing 11 which can be constructed of brushed stainless steel, other metals, or appropriately hardened plastics capable of withstanding vibration without cracking or breaking.

At the end of the tool 10 is a receptacle 12 adapted to receive and retain a brush 13 mounted on a wooden dowel 14, or other attachment for the dental arts, such as a small spatula of metal or the like for applying ceramic material to substrates.

Preferably, tool 10 has a roughened area 15 encircling the tool near the brush tip end thereof. Area 15 is adapted to ensure a sure grip on the tool by the operator, and to provide an ideal surface with which to contact the substrate to which ceramic is being applied for the purpose of transmitting vibrations from the tool 10 to the substrate to cause the ceramic to flow over the substrate in an even layer. Such a roughened area can be achieved by cross-hatching the stainless steel housing at that point or by other means known in the art for roughing metallic or plastic surfaces.

Interiorly of tool 10, as best illustrated in FIG. 2, a vibrational source, preferably an electromagnet 16, is mounted near the rear of the tool 10 for maximum balance in the hand of the operator. Electromagnet 16 is in contact at the rearward side with a vibrational plate 17 disposed within housing 11. Plate 17 is connected to one end of an elongate rod 18 at the forward side of the plate 17. Rod 18 extends internally of housing 11 forward to connect to a collar 19. Collar 19 in turn is in contact with the end of dowl 14. Vibrations are transmitted from electromagnet 16 to plate 17, and thence through rod 18 to collar 19 and the attachment such as a brush 13 at the tip of the tool.

Spring biasing means 20 are preferably disposed circumferentially of the rod between electromagnet 16 and a block portion 21 within housing 11. Such spring biasing means 20 acts in concert with a screw-type urging means 22 extending against spring biasing means 23 through an aperture 24 in a cap 25 at the rear of the tool in contact with plate 17 to adjust the tension on the plate 17, and accordingly, the degree or level of vibration imported to the tool 10 and the brush 13. Screw means 22 can be adjusted by hand by means of the small knob 26 or screw means 22 which extends externally of housing 11. As plate 17 is urged forward by the manual rotations of screw means 22 against electromagnet 16 and spring biasing means 20 proportionately less vibration is imparted to the tool and brush attachment. With the loosening of the screw means 22, proportionately more vibration is imparted.

Electromagnet 16 can be connected by power line 27 to an electrical source (not shown) through appropriate switching means, such as a foot rheostat.

Whereas, this invention has been described herein with respect to a preferred embodiment it is to be understood that alternative constructions are contemplated and will be obvious to one skilled in the art, all of which are defined within the scope of the appended claims.

I claim:

1. A method for creating dental prosthetic appliances comprising the steps of:
   - adhering a pre-determined amount of dental prosthetic-forming material to the vibrating brush means of a vibrating dental tool;
   - applying said dental prosthetic-forming material to a substrate with said dental tool; and
   - shaping said material into said substrate to form a dental prosthetic appliance with said vibrating brush means.

2. A method as set forth in claim 1, wherein said dental prosthetic-forming material is applied to a substrate with spatula means, and said prosthetic appliance is shaped with said brush means.

3. A method as set forth in claim 1, wherein said dental prosthetic appliance is shaped with vibrating spatula means of a vibratory dental tool.

4. A method as set forth in claim 1, wherein said dental prosthetic-forming material is applied to said substrate an applicator, and then shaped into a dental prosthetic appliance with said vibrating brush means of the vibratory dental tool.

* * * * *